US005843929A

United States Patent [19]
Larson et al.

[11] Patent Number: 5,843,929
[45] Date of Patent: Dec. 1, 1998

[54] CHEMOPREVENTION OF METACHRONOUS ADENOMATOUS COLORECTAL POLYPS

[75] Inventors: Mark V. Larson, Elgin; David A. Ahlquist; Randall K. Pearson, both of Rochester, all of Minn.

[73] Assignee: Mayo Foundation for Medical Education and Research, Rochester, N.Y.

[21] Appl. No.: 621,781

[22] Filed: Mar. 22, 1996

[51] Int. Cl.⁶ .................................................... A61K 31/56
[52] U.S. Cl. .......................................... 514/182; 514/171
[58] Field of Search ............................................ 514/182

[56] References Cited

PUBLICATIONS

"Sulindac", Physician's Desk Reference, Medical Economics Data, Montvale, NJ, 1483–1486, (1993).
I. Ahnfeldt–Rhonne, et al., "Clinical Evidence Supporting the Radical Scavenger Mechanism of 5–Aminosalicylic Acid", Gastroenterology, 98, 1162–1169, (1990).
I. Ahnfeldt–Rhonne, "Rationales for Drug Development in Inflammation: Eicosanoids and Oxygen–derived Free Radicals", Danish Med. Bull., 38, 291–303, (1991).
H. Allgayer, et al., "Is Radical Scavenging Necessary in the Treatment of Inflammatory Bowel Disease", Gastroenterology, 100, 581–582, (1991).
H. Allgayer, et al., "Superoxide, Hydroxyl and Fatty Acid Radical Scavenging by Aminosalicylates", Biochem. Pharm., 43, 259–262, (1992).
H. Allgayer, et al., "Superoxide Inhibition Following Different Stimuli of Respitory Burst and Metabolism of Aminosalicylate in Neutrophils", Dig. Dis. & Sci., 39, 145–151, (1994).
W. H. Bachrach, et al., "Ursodeoxycholic Acid in the Treatment of Cholesterol Choleithiasis", Dig. Dis. Sci., 27, 833–856, (1982).
B. I. Cohen, et al., "The Role of Bile Acids in Colorectal Carcinogenesis", In: Colorectal Cancer: From Pathogenesis to Prevention?, Seitz HK et al., eds., New York, Springer–Verig., 125–138, (1989).
P. Czygan, et al., "Chenodeoxycholic Acid But Not Ursodeoxycholic Acid Enhances Colonic Carcinogenesis in the Rat", Bile Acids and Cholesterol in Health and Disease, Ed. Paumgartner et al., MTP Press Limited, Lancaster, England, 393–395, (1983).
T. C. Dinis, et al., "Actin of Phenolic Derivatives (Acetominophen, Salicylate, and 5–aminosalicylate) as Inhibitors of Membrane Lipid Peroxidation and as Peroxyl Radical Scavengers", Arch. Bioc. Biop., 315, 161–169, (1994).
D. E. Duggan, et al., "The Disposition of Sulindac", Clin. Pharmacol. Ther., 21, 326–335, (1977).
E. R. Fearon, et al., "Clonal Analysis of Human Colorectal Tumors", Science, 238, 193, (1987).
A. Fischer–Nielsen, et al., "8–Hydroxydeoxyguanosine in vitro: Effects of Glutathione, Ascorbate, and 5–Aminosalicylic Acid", Free Radical Biol. Med., 13, 121–126, (1992).

A. Fischer–Nielsen, et al., "Radiation Induced Formation of 8–hydroxy–2'–deoxyguanosine and Its Prevention by Scavengers", Carcinogenesis, 15, 1609–1612, (1994).
C. Fischer, et al., "Radical–derived Oxidation Products of 5–aminosalicylic Acid and N–acetyl–5–aminosalicylic Acid", J. Chromat. B: Biomed. Appl., 661, 57–68, (1994).
T. S. Gaginella, et al., "Sulfasalazine Multiplicity of Action", Dig. Dis. Sci., 37, 801–812, (1992).
P. Gionchetti, et al., "Scavenger Effect of Sulfasalazine, 5–Aminosalicylic Acid, and Olsalazine on Superoxide Radical Generation", Dig. Dis. Sci., 36, 174–178, (1991).
S. M. Greenfield, et al., "The Effects of 5–aminosalicylic Acid and Acetyl–5–aminosalicylic Acid on Lipid Peroxidation in Erythrocytes and Prostaglandin Production by Mononuclear Cells", Aliment. Pharmacol. Ther., 6, 671–683, (1992).
V. Gross, et al., "Free Radicals in Inflammatory Bowel Diseases Pathophysiology and Therapeutic Implications", Hepato–Gastroenterol., 41, 320–327, 1994.
M. J. Hill, "Bile Flow and Colon Cancer", Mutation Review, 238, 313–320, (1990).
M. J. Hill, "From Adenoma to Carcinoma of the Colorectum", Recent Results Cancer Res., 122, 71–84, (1991).
A. F. Hofman, "Chemistry and Enterohepatic Circulation of Bile Acids", Hepatology, , 4s–14s, (1984).
A. F. Hofmann, "Pharmacology of Chenodeoxycholic and Ursodeoxycholic Acid in Man", Bile Acids and Cholesterol in Health and Disease, Ed. Paumgartner, G. et al., MTP Press Limited, Lancaster, England, 301–337, (1983).
H. B. Hucher, et al., "Studies on the Absorbtion, Distribution and Excretion of Indomethacin in Various Species", J. Pharmacol. Exp. Ther., 153, 237–239, (1966).
S. M. Huijghebaert, et al., "Influence of the Amino Acid Moiety of Deconjugation of Bile Acid Amidates by Cholyglycine Hydrolase of Human Fecal Cultures", J. Lipid Res., 27, 742–752, (1986).
D. Labayle, et al., "Sulindac Causes Regression of Rectal Polyps in Familial Adenomatous Polyposis", Gastroenterology, 101, 635–639, (1991).
A. M. Miles, et al., "Antioxidant Properties of 5–aminosalicylic Acid: Potential Mechanism for Its Protective Effect in Ulcerative Colitis", Advances in Mucosal Immunology, Part B, Ed. Mestecky et al., Plenum Press, New York, 1317–1321, (1995).
M. Moorghen, et al., "The Protective Effect of Sulindac Against Chemically–induced Primary Colonic Tumors in Mice", J. Pathol., 156, 341–347, (1988).

(List continued on next page.)

Primary Examiner—Jerome D. Goldberg
Attorney, Agent, or Firm—Schwegman, Lundberg, Woessner, & Kluth, P.A.

[57] ABSTRACT

A method for protecting a colorectum against a recurrence of adenomomas is provided, wherein ursodeoxycholic acid, or ursodeoxycholic acid in combination with sulindac, is administered to a patient afflicted with colorectal adenomas in an amount effective to prevent the recurrence of colorectal adenomas following the removal thereof.

3 Claims, No Drawings

OTHER PUBLICATIONS

T. Narisewa, et al., "Inhibition of Development of Methylnitrosourea–induced Rat Colon Tumors by Indomethacin Treatment", *Cancer Research, 41,* 1954–1957, (1981).

H. Nava, et al., "Follow–up Colonoscopy in Patients with Colorectal Adenomatous Polyps", *Dis. Colon Rectum, 30,* 465, (1987).

M. G. Neuman, et al., "Effect of Tauroursodeoxycholic and Ursodeoxycholic Acid on Ethanol–induced Cell Injuries in the Human Hep G2 Cell Line", *Gastroenterology, 109,* 555–563, (1995).

M. L. Nicholson, et al., "Increased Cell Membrane Arachidonic Acid in Experimental Colorectal Tumors.", *Gut, 32,* 413–418, (1991).

O. H. Nielsen, et al., "Effect of 5–aminosalicylic Acid and Analogous Substances on Superoxide Generation and Intracellular Free Calcium in Human Neutrophilic Granulocytes", *Gastroenterology, 28,* 527–532, (1993).

H. W. Olsen, et al., "Review of Recurrent Polyps in Cancer in 500 Patients with Initial Colonoscopy of Polyps", *Dig. Colon Rectum, 31,* 222–227, (1988).

A. Paganini–Hill, et al., "Aspirin Use in Incidence of Large–bowel Cancer in a California Retirement Community", *J. Nat. Cancer Inst., 83,* 1182–1183, (1991).

M. Pollard, et al., "The Suppresive Effect of Paroxican on Autochthonous Intestinal Tumors in the Rat", *Cancer Letters, 21,* 57–61, (1983).

R. E. Poupon, et al., "A Multicenter, Controlled Trial of Ursodiol for the Treatment of Primary Biliary Cirrhosis", *N. Eng. J. Med., 324,* 1548–1554, (1991).

B. S. Reddy, et al., "Promoting Effect Of Bile Acids in Colon Carcinogenesis in Germ–free and Conventional F344 Rats", *Cancer Res., 37,* 3238–3242, (1977).

J. Rigau, et al., "Effects of Long–term Sulindac Therapy on Colonic Polyposis", *Annals of Internal Med., 115,* 952–955, (1991).

C. MP. Rodrigues, et al., "Tauroursodeaxycholate Increases Rat Liver Ursodeoxycholate Levels and Limits Lithocholate Formation Better Than Ursodeoxycholate", *Gastroenterology, 109,* 564–572, (1995).

L. Rosenberg, et al., "A Hypothesis: Nonsteroidal Anti–Inflammatory Drugs Reduce the Incidence of Large Bowel Cancer", *J. Nat. Cancer Inst., 83,* 355–358, (1991).

A. N. Sarwal, et al., "Effects of Dietary Administration of Chenodeoxycholic Acid on N–Methyl–N–Notrosourea–Induced Colon Cancer in Rats", *Bioc. Biophys. Acts, 574,* 423–432, (1979).

H. Tamai, et al., "Scavenging Effect of 5–aminosalicylic Acid on Neutrophil–derived Oxidants", *Biochem. Pharm., 41,* 1001–1006, (1991).

N. Tanida, et al., "Effects of Oral Administration of Sulfolithocholic Acid Disodium Salt and Lithocholid Acid Sodium on N–Methyl–N–Nitrosourea–Induced Colonic Tumorogenesis in Conventional Rats", *Cancer Res., 49,* (1989).

M. J. Thun, et al., "Aspirin Use and Reduced Risk of Fatal Colon Cancer", *New Eng. J. Med., 323,* 1593–1596, (1991).

W. R. Waddell, et al., "Sulindac for Polyposis of the Colon", *Am. J. of Surgery,* 157, 175–179, (1989).

W. R. Waddell, et al., "Sulindac for Polyposis of the Colon", *J. of Surgical Onc.,* 24, 83–87, (1983).

C. B. Williams, et al., "The St. Marks's Neoplastic Polyp Follow–up Study", *Front Gastrointest. Res., 10,* 226, (1986).

S. J. Winawer, et al., "Randomized Comparison of Surveillance Intervals After Colonoscopic Removal of Newly Diagnosed Adenomatous Polyps", *N. Eng. J. Med., 328,* 901–906, (1993).

T. Yamada, et al., "The Effects of Sulfasalazine Metobolites on Hemoglobin–catalyzed Lipid Peroxidation", *Free Radical Biol Med., 10,* 41–49, (1991).

5,843,929

CHEMOPREVENTION OF METACHRONOUS ADENOMATOUS COLORECTAL POLYPS

BACKGROUND OF THE INVENTION

Colorectal cancer is the most common visceral cancer in the United States. Each year, more than 160,000 new cases of colorectal cancer are detected which account for more than 60,000 deaths. The national incidence of colorectal cancer appears to be on the rise, as, it increased by 9.4% from 1973 to 1986 based on a sample of 10% of the U.S. population. Unfortunately, the five-year survival rate has not improved significantly over the past four decades. As prognosis worsens with more advanced cancers, many physicians and several national medical societies advocate routine screening to increase early stage detection. However, while the rationale for screening is sound, such efforts at secondary prevention require an enormous use of medical resources and have not been shown to be effective in a general population.

Colorectal cancer provides unique opportunities for primary intervention among human malignancies because it progresses through clinically recognizable stages from normal mucosa through enlarging and increasingly dysplastic polyps which eventuate in carcinoma. Support for the adenoma to carcinoma sequence is provided by epidemiological studies, shared genetic properties of both adenomas and carcinomas, and the natural history of adenomas as observed in patients with familial adenomatous polyposis. Nicholson M L, et al., "Increased Cell Membrane Arachidonic Acid in Experimental Colorectal Tumors," *Gut* 32:413–8 (1991); Fearon E R, et al., "Colonal Analysis of Human Colorectal Tumors," *Science* 238:193 (1987); and Bussey H J R, "Familial Polyposis Coli," *Family Studies, Histopathology, Differential Diagnosis, and Results of Treatment* (Johns Hopkins University Press, Baltimore 1975). Genetic factors appear to mediate the development of colonic adenomas in familial adenomatous polyposis (FAP), for example, and may also play a role in the development of sporadic adenomas and carcinomas. In addition, there is evidence for an accumulating series of genetic deletions and mutations including known oncogenes and tumor suppressors, that accompany the transition from normal mucosa to adenoma to carcinoma.

The precursor relationship of colorectal adenoma to carcinoma and the high prevalence of adenomas makes them an attractive target in chemoprevention trials. The prevalence increases with age in moderate and high risk populations, reaching 20–40% at the age of 50–60 years, and 50% or more for individuals older than 70 years. The steepest increase in adenoma prevalence occurs between the ages of 50–59. However, removal of polyps does not change the pathogenetic milieu responsible for their growth and development. The recurrence rate for colorectal adenomas has been variably reported, but most studies document an adenoma recurrence rate of 20–60% by two years. Nava H, et al., "Follow-up Colonoscopy in Patients With Colorectal Adenomatous Polyps," *Dis. Colon Rectum* 30:465 (1987); Olsen H W, et al., "Review of Recurrent Polyps in Cancer in 500 Patients With Initial Colonsocopy for Polyps," *Dis. Colon Rectum* 31:222–227 (1988); Williams C B and Macrae F A, "The St. Mark's Neoplastic Polyp Follow-up Study," *Front. Gastrointest. Res.* 10:226 (1986). Winawer recently reported that 28% of patients who had newly diagnosed adenomas removed by colonoscopy had additional polyps detected at a one-year follow-up examination, and of those patients, 22% had new adenomatous polyps again detected on examination two years later. Winawer S J, et al., "Randomized Comparison of Surveillance Intervals After Colonoscopic Removal of Newly Diagnosed Adenomatous Polyps," *New Engl. J. Med.* 328:901–6 (1993). Patients who have undergone surgical resection of a primary colorectal cancer have also been shown to be at high risk of developing metachronous adenomas. Olsen H W, et al., "Review of Recurrent Polyps in Cancer in 500 Patients With Initial Colonsocopy for Polyps," *Dis. Colon Rectum* 31:222–227 (1988).

Several studies have focused attention on bile acids as a potential mediator of the dietary influence on colorectral cancer risk. Hofmann A F, "Chemistry and Enterohepatic Circulation of Bile Acids," *Hepatology* 4S–14S (1984). Bile acids are important detergents for fat solubilization and digestion in the proximal intestine. Specific transport processes in the apical domain of the terminal ileal enterocyte and basolateral domain of the hepatocyte account for the efficient conservation in the enterohepatic circulation. Only a small fraction of bile acids enter the colon; however, perturbations of the cycling rate of bile acids by diet (e.g., fat) or surgery (e.g., cholecystectomy) may increase the fecal bile acid load and perhaps account for the associated increased risk of colon cancer. Hill M J, "Bile Flow and Colon Cancer," *Mutation Review* 238:313–320 (1990). Studies linking perturbations in fecal bile acids with human colon cancer, however, have been inconsistent and controversial. The inconsistencies could stem from differences in the populations studied, patient selection, or methodologic artifacts in measuring fecal bile acid excretion.

Thus, chemoprevention of colorectal cancer, by dietary or pharmacologic intervention, remains to be established. There is a continuing need, therefore, to develop new chemopreventative treatments for colorectal adenomas.

SUMMARY OF THE INVENTION

The present invention provides a method for preventing a recurrence of colorectal adenomas in a human patient afflicted with such adenomas comprising administering ursodeoxycholic acid, or a pharmaceutically-acceptable salt thereof, in an amount effective to prevent the recurrence of colorectal adenomas following removal thereof. A dose of about 50 to 7500 mg per day of ursodeoxycholic acid is preferably administered to the patient. More preferably, the dose is about 200 mg to 5000 mg. For example, in the working examples presented hereinbelow, the dose is at about 750 mg to 1500 mg per day. The ursodeoxycholic acid is preferably administered orally.

The present method optionally further comprises administering a nonsteroidal anti-inflammatory agent, or a pharmaceutically-acceptable salt thereof, in combination with the administration of ursodeoxycholic acid to prevent the recurrence of colorectal adenomas. Preferably, the nonsteroid anti-inflammatory agent is sulindac, or a pharmaceutically acceptable salt thereof. Sulindac can be administered orally at a dose of about 10 mg to 1500 mg per day. Preferably, sulindac is administered at a dose of about 50 mg to 500 mg per day. More preferably the sulindac is orally administered at a dose of about 150 mg to 300 mg per day.

As used herein with respect to the present method, the term "afflicted with" encompasses a patient at risk of recurrence or development of colorectal adenomas, as well as a patient who has developed said adenomas, and who is at risk for recurrence or progression of the condition.

DETAILED DESCRIPTION OF THE INVENTION

Ursodeoxycholate (URSO) is the hydrophilic 7-beta epimer of chenodeoxycholate, notable for its lack of cytotoxicity in a variety of model cell systems, including colonic epithelia. As a drug, it is rapidly absorbed from the proximal small intestine, extracted by the liver, conjugated and secreted, whereupon it enters the enterohepatic circulation. These properties have led to its clinical use in gallstone dissolution and as proposed treatment in the chronic cholestatic cholangiopathies, primary biliary cirrhosis and sclerosing cholangitis. While the precise mechanism of its benefit in these clinical conditions is unknown, URSO apparently alters the lithogenicity or cytotoxicity of bile.

URSO has the advantage of being virtually free of side effects. Doses of ursodeoxycholate at 15 mg/kg/day used in primary biliary cirrhosis trials were extremely well tolerated and without toxicity. Poupon R E, et al., "A Multicenter, Controlled Trial of Ursodiol for the Treatment of Primary Biliary Cirrhosis," *New Engl. J Med.* 324:1548–1554 (1991). An extensive review of the use of URSO in clinical trials revealed that treatment with URSO resulted in 1) an infrequent, transient elevation of hepatic transaminases, 2) a frequent reduction in serum triglycerides, and 3) a transient, mild diarrhea in 3% of patients (range=0–9% of patients) that resolved spontaneously without dose reduction. Bachrach W H and Hofmann A F, "Ursodeoxycholic Acid in the Treatment of Cholesterol Cholelithiasis," *Dig. Dis. Sci.* 27:833–856 (1982). Doses of up to 22–25 mg/kg/day can be well-tolerated. Further, the drug can be administered in a single daily dose, which can lead to improved compliance over multiple, divided doses.

Nonsteroid anti-inflammatory drugs (NSAIDs), such as sulindac, can inhibit the neoplastic transformation of colorectal epithelium. Several mechanisms may explain their chemopreventive effect, including inhibition of prostaglandin synthesis, of growth factors, or of genetic mutations that ultimately lead to colorectal cancer. As of yet, however, the exact mechanism(s) remains to be established.

All NSAIDs inhibit cyclooxygenase, the enzyme that converts arachidonic acid to prostaglandins and thromboxanes. Patients receiving relatively low doses of NSAIDs (e.g., piroxicam, 7.5 mg/day) have shown a sustained, significant reduction (>20%) in colorectal mucosal $PGE_2$ concentrations. Earnest D L, et al., "NSAIDs for Prevention of Colon Cancer; Early Studies with Piroxicam in Humans," Presented at *Fourth International Conference on Prevention of Human Cancer: Nutrition in Chemoprevention Controversies* (June 3–6, 1992). Immune surveillance is also enhanced by drugs such as NSAIDs that reduce $PGE_2$ synthesis. Id. Thus, prostaglandin inhibition can potentially suppress abnormal proliferation of colorectal epithelium and progression toward dysplastic lesions.

Indomethacin, piroxicam, and sulindac have all been shown to inhibit carcinogen-induced colonic tumors in rodents. Narisewa T, et al., "Inhibition of Development of Methylnitrosourea-Induced Rat Colon Tumors by Indomethacin Treatment," *Cancer Research* 41:1954–1957 (1981); Pollard M, et al., "The Suppressive Effect of Paroxican on Autochthonous Intestinal Tumors in the Rat," *Cancer Letters* 21:57–61 (1983); Moorghen M, et al. "The Protective Effect of Sulindac Against Chemically-Induced Primary Colonic Tumors in Mice," *J. Pathol.* 156:341–347 (1988). In humans, however, indomethacin achieves relatively low colonic concentrations, and has not been shown to inhibit or induce regression of colonic polyps. Hucher H B, et al., "Studies on the Absorption, Distribution, and Excretion of Indomethacin in Various Species," *J. Pharmacol. Exp. Ther.* 153:237–299 (1966).

The most dramatic example of abnormal colonic proliferation occurs in familial adenomatous polyposis (FAP), a relatively rare genetic disorder that manifests an extraordinary number of adenomatous colonic polyps and resulting cancers in affected individuals. Since 1983, there have been numerous published reports that have described moderate to marked polyp regression in FAP patients treated with sulindac for up to six months. Waddell W R and Longhry R W, "Sulindac for Polyposis of the Colon," *J Surg. Onc.* 24:83–87 (1983); Labayle D, et al., "Sulindac Causes Regression of Rectal Polyps in Familial Adenomatous Polyposis," *Gastroenterology* 101:635–639 (1991); Rigau J, et al., "Effects of Long-Term Sulindac Therapy on Colonic Polyposis" *Annals of Internal Medicine* 115:952–954 (1991); Waddell W R, et al., "Sulindac for Polyposis of the Colon," *Am. J Surg.* 157:175–179 (1989). This effect occurred both in patients with only residual rectal mucosa (following total colectomy) and in patients with diffuse colonic polyposis. Polyp regression was typically rapid, however, polyps recurred relatively quickly after stopping sulindac.

The potential chemopreventive benefits of sulindac or any other NSAID used as a single agent is tempered by their well-known toxicities and moderately high risk of intolerance. Abdominal pain, dyspepsia, nausea, diarrhea, constipation, rash, dizziness, or headache have been reported in 3–9% of patients. Physician's Desk Reference, pp. 1433–1435 (Medical Economics Company, 1993). Toxicities reported in 1–3% of patients include flatulence, anorexia, gastrointestinal cramps, puritus, nervousness, tinnitus, and edema. A large number of other toxicities have been reported associated with sulindac in less than 1% of cases, including renal and hepatic toxicity, and gastrointestinal bleeding. NSAIDs have been increasingly recognized as an important cause of peptic ulceration. The elderly appear to be especially vulnerable, as the incidence of NSAID-induced gastroduodenal ulcer disease, including gastrointestinal bleeding, is higher in those over age 60; this is also the age group most likely to develop colorectal cancer, and therefore, most likely to benefit from chemoprevention.

The amount of URSO or sulindac required for use in treatment varies not only with the particular form of URSO or sulindac but also with the severity of the symptoms being treated and the age and condition of the patient. For human dosage, effective amounts of URSO would fall generally in the range of 50 to 7500 mg per day of ursodeoxycholic acid for adult patients. Preferably, the dose is about 200 mg to 5000 mg of URSO per day. More preferably, the dose is about 750 mg to 1500 mg URSO per day. Effective amounts of sulindac can be administered at a dose of about 10 mg to 1500 mg per day. Preferably, sulindac is administered at a dose of about 50 mg to 500 mg per day. More preferably the sulindac is administered at a dose of about 150 mg to 300 mg per day. Compositions of this invention may be administered one or more times daily.

The pharmaceutically acceptable salts of the biologically active compounds may include carboxylic acid salts, such as alkali metal carboxylates and quaternatery ammonium salts. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Although the compounds of the present invention and/or its salts may be administered as the pure chemicals, it is preferable to present the active ingredient as a pharmaceutical composition. Pharmaceutical compositions comprising unit dosage forms of URSO, sulindac or salts thereof in combination with a pharmaceutically acceptable carrier are commercially available or may be prepared from standard ingredients using standard techniques. The invention thus further provides a pharmaceutical composition comprising one or more of the claimed compounds and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The typical acceptable pharmaceutical carriers for use in oral formulations are exemplified by sugars as lactose, sucrose, mannitol, and sorbitol; starches such as corn starch, tapioca starch, and potato starch; cellulose and derivatives such as sodium carboxymethyl cellulose, ethyl cellulose, and methyl cellulose; calcium phosphates such as dicalcium phosphate and tricalcium phosphate; sodium sulfate, calcium sulfate; polyvinyl pyrrolidone, polyvinyl alcohol, stearic acid, alkaline earth metal stearates such as magnesium stearate and calcium stearate; vegetable oils such as peanut oil, cottonseed oil, sesame oil, olive oil, and corn oil; nonionic, cationic and anionic surfactants; ethylene glycol polymers; beta-cyclodextrin; fatty alcohols and hydrolyzed cereal solids; as well as other non-toxic compatible fillers, binders, disintegrants, buffers, antioxidants, lubricants, flavoring agents, and the like commonly used in pharmaceutical formulations.

The compounds according to the invention may also be formulated for parenteral administration (e.g., by injection, for example, bolus injection or continuous infusion) and may be presented in unit dose form in ampules, pre-filled syringes, small bolus infusion containers or in multi-doses containers with an added preservative. The compositions may take such forms as suspensions, solutions, or emulsions in oily or aqueous vehicles, and may contain formulatory agents such as suspending, stabilizing and/or dispersing agents. Injectable formulations use aqueous physiologically acceptable carriers, e.g., distilled water, and preferably contain a compatible buffer system selected to maintain the pH in the desired range of 6.5 to 8, preferably about 7.0 to 7.4. A typical buffer system is a combination of sodium dibasic phosphate and sodium monobasic phosphate. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds of the present invention may be formulated as ointments, creams or lotions, or as the active ingredient of a transdermal patch. Suitable transdermal delivery systems are disclosed, for example, in Fisher et al. (U.S. Pat. Nos. 4,788,603) or Bawas et al. (U.S. Pat. Nos. 4,931,279, 4,668,504 and 4,713,224) or Chien et al. (U.S. Pat. Nos. 4,818,540, 5,296,230, and 5,045,319). When desired, the above-described compositions can be adapted to provide sustained or prolonged release of the active ingredient employed, e.g., by combination thereof with certain hydrophilic polymer matrices, e.g., comprising natural gels, synthetic polymer gels or mixtures thereof.

Ointments and creams may, for example, be formulated with an aqueous or oily base with the addition of suitable thickening and/or gelling agents, such as gelatin, vegetable oils, polyalkylene glycol, or alcohol. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4383,529, or 4,051,842. Topical compositions may also include standard liquid formulations, e.g., distilled water or physiological saline solutions, in combination with nontoxic thickeners and preservatives.

Compositions suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The following examples are intended to illustrate but not limit the invention.

EXAMPLE 1

A total of 900 patients are recruited to study the chemopreventative effects of ursodeoxycholic acid (URSO) to prevent the recurrence of metachronous adenomatous colorectal polyps. The study patients are male and female, age 50 and older who have had complete endoscopic or surgical resection of a histologically verified colorectal adenoma (at least 5 mm in size) or early-stage carcinoma (Duke's A or B1) resulting in a neoplasm-free colorectum, within three months prior to entering the study. The study patients must have an intact rectum and more than half of the colorectum remaining.

The patients are divided into three treatment groups. The treatment groups, defined by the dosages of sulindac and URSO, are shown below:

| Placebo | 750 mg q/d URSO | 750 mg b.i.d. URSO |
| --- | --- | --- |
| n = 300 | n = 300 | n = 300 |

To ensure that both the patient and the medical professionals who care for the patient are blind to the identity of the treatment assignment, only the study coordinator and the study group statisticians have access to the uncoded list of patients' identification numbers and their treatment assignments. In addition, all patients take the same number of pills each day (active drug, placebo or both). Patients take the URSO tablets (250 mg) or its placebo orally twice a day with meals for about one year. URSO and placebo are available from Axcan Pharma (Interfalk, Canada Inc., Quebec, Canada).

One year after initiating the study, each patient receives a follow-up coloscopic examination. Following sedation with intravenous midazolam and/or a narcotic at doses deemed appropriate by the colonoscopist, the rectum is intubated and the colonoscope advanced to the cecum in the usual fashion. Upon withdrawal of the colonoscope, all neoplastic lesions are identified, and their location and size recorded. All neoplastic lesions visualized are removed in the usual fashion, using the electrocautery snare or hot biopsy-forceps technique. The colonoscopist documents (1) whether a complete or a limited examination was performed, (2) the quality of the preparation, and (3) whether or not all visualized polypoid tissue was removed.

The primary endpoint of the study is the recurrence of polyps considered as a dichotomous outcome. A logistic regression for polyp recurrence (yes/no) at one year is used to assess treatment effects. Distributions of polyp size and number is determined for and compared among randomized groups. Although the randomization procedure should result in balanced treatment groups, the stratification factors and a few other variables (e.g., size, number of index polyps) thought to be associated with recurrence of polyps are included as covariates in the logistic regression model. Patients who "drop out" during the follow-up period (either due to toxicity or non-compliance) are considered as treatment failures (recurrent polyps), based on an "intent to treat" philosophy. The incidence of toxicity and compliance rates for each treatment arm is estimated, and the rates are compared among the treatment groups using a logistic regression analysis.

Summaries of the distribution of primary and secondary outcomes done by each stratification factor separately, is tabulated using means and standard errors, medians, and inter-quartile range, or percentages, as appropriate for continuous or discrete data. Distributions of primary and secondary endpoints is also tabulated separately by sex and by ethnic/racial minority status.

EXAMPLE 2

A total of 1200 patients are recruited to study the chemopreventative effects of ursodeoxycholic acid (URSO), the nonsteroid anti-inflammatory drug (NSAID) sulindac, or URSO in combination with sulindac, to prevent the recurrence of metachronous adenomatous colorectal polyps. The study patients are male and female, age 50 and older who have had complete endoscopic or surgical resection of a histologically verified colorectal adenoma (at least 5 mm in size) or early-stage carcinoma (Duke's A or B1) resulting in a neoplasm-free colorectum, within three months prior to entering the study. The study patients must have an intact rectum and more than half of the colorectum remaining.

The patients are divided into nine treatment groups. The treatment groups, defined by the dosages of sulindac and URSO, are shown below:

|  | Placebo BID | 750 mg qd URSO | 750 mg BID URSO | TOTAL |
| --- | --- | --- | --- | --- |
| Placebo BID | n = 150 | n = 100 | n = 150 | 400 |
| 150 mg qd Sulindac | n = 100 | n = 200 | n = 100 | 400 |
| 150 mg BID Sulindac | n = 150 | n = 100 | n = 150 | 400 |
| TOTAL | 400 | 400 | 400 | 1200 |

The factorial design recruits 1200 total patients randomized as shown per cell, yielding 400 patients per dosage group for each study drug.

To ensure that both the patient and the medical professionals who care for the patient are blind to the identity of the treatment assignment, only the study coordinator and the study group statisticians have access to the uncoded list of patients' identification numbers and their treatment assignments. In addition, all patients take the same number of pills each day (active drug(s), placebo, or both). Patients take the sulindac tablets (150 mg) or its placebo orally twice a day with meals for about one year. The URSO tablets (250 mg) or its placebo are also taken orally twice a day with meals for about one year. Sulindac and its matching placebo are available from Merck Sharp and Dohme (West Point, Pa.). URSO and placebo are available from Interfalk (Quebec, Canada).

One year after initiating the study, each patient receives a follow-up coloscopic examination. Following sedation with intravenous midazolam and/or a narcotic at doses deemed appropriate by the colonoscopist, the rectum is intubated and the colonoscope advanced to the cecum in the usual fashion. Upon withdrawal of the colonoscope, all neoplastic lesions are identified, and their location and size recorded. All neoplastic lesions visualized are removed in the usual fashion, using the electrocautery snare or hot biopsy-forceps technique. The coloscopist documents (1) whether a complete or a limited examination was performed, (2) the quality of the preparation, and (3) whether or not all visualized polypoid tissue was removed.

The primary endpoint of the study is the recurrence of polyps considered as a dichotomous outcome. A logistic regression for polyp recurrence (yes/no) at one year is used to assess treatment effects. Distributions of polyp size and number is determined for and compared among randomized groups. Although the randomization procedure should result in balanced treatment groups, the stratification factors and a few other variables (e.g., size, number of index polyps) thought to be associated with recurrence of polyps are included as covariates in the logistic regression model. Patients who "drop out" during the follow-up period (either due to toxicity or non-compliance) are considered as treatment failures (recurrent polyps), based on an "intent to treat" philosophy. The incidence of toxicity and compliance rates for each treatment arm is estimated, and the rates are compared among the treatment groups using a logistic regression analysis.

Summaries of the distribution of primary and secondary outcomes done by each stratification factor separately, is tabulated using means and standard errors, medians, and inter-quartile range, or percentages, as appropriate for continuous or discrete data. Distributions of primary and secondary endpoints is also tabulated separately by sex and by ethnic/racial minority status.

NSAIDs are ubiquitous, are available in over-the-counter preparations as well as prescription varieties, and are often used to treat a wide spectrum of symptoms and diseases. In order to prevent contamination of groups by the inadvertent use of an NSAID, patients are given a list of NSAIDs, as well as a list of over-the-counter medications that contain an NSAID (e.g., Darvon contains aspirin). Patients are instructed to avoid these agents (Tylenol may be used). If the prolonged use of an NSAID is medically necessary, the patient is disqualified from the study.

All publications are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method for protecting a colorectum against a recurrence of colorectal adenomas comprising administering to a human afflicted with colorectal adenomas, an amount of ursodeoxycholic acid or a pharmaceutically acceptable salt thereof, effective to prevent the recurrence of colorectal adenomas following the removal thereof.

2. The method of claim 1 wherein the effective amount of ursodeoxycholic acid or pharmaceutically acceptable salt thereof is administered orally.

3. The method of claim 2 wherein ursodeoxycholic acid is administered at a dose of about 50 to 7500 mg per day.

* * * * *